United States Patent [19]
Aita et al.

[11] Patent Number: 5,925,033
[45] Date of Patent: *Jul. 20, 1999

[54] METHOD FOR INTRA-OPERATIVE MYOCARDIAL REVASCULARIZATION

[75] Inventors: Michael Aita, Sunnyvale, Calif.; Mahmood Mirhoseini; Mary Cayton, both of Glendale, Wis.; Carl J. Simpson; Brian Guscott, both of Los Altos Hills, Calif.

[73] Assignee: Cardiogenesis Corporation, Santa Clara, Calif.

[ * ] Notice: This patent is subject to a terminal disclaimer.

[21] Appl. No.: 08/550,559

[22] Filed: Oct. 31, 1995

Related U.S. Application Data

[63] Continuation of application No. 08/361,787, Dec. 20, 1994, Pat. No. 5,554,152, which is a continuation of application No. 08/079,699, Jun. 16, 1993, Pat. No. 5,380,316, which is a continuation of application No. 07/630,259, Dec. 18, 1990, abandoned.

[51] Int. Cl.$^6$ .................................................. A61N 5/06
[52] U.S. Cl. ................................ 606/7; 128/898; 606/15
[58] Field of Search ........................ 606/2, 3, 7, 10–18; 607/88, 89; 128/898

[56] References Cited

U.S. PATENT DOCUMENTS

| | | | |
|---|---|---|---|
| 4,469,098 | 9/1984 | Davi | 606/7 |
| 4,658,817 | 4/1987 | Hardy | 606/7 |
| 4,669,467 | 6/1987 | Willett et al. | 606/15 |
| 4,860,743 | 8/1989 | Abela | 606/16 X |
| 4,890,898 | 1/1990 | Bentley et al. | 606/16 X |
| 4,917,084 | 4/1990 | Sinofsky | 606/7 |
| 4,967,745 | 11/1990 | Hayes et al. | 606/15 X |
| 4,985,029 | 1/1991 | Hoshino | 606/16 |
| 5,037,421 | 8/1991 | Boutacoff et al. | 606/15 |
| 5,093,877 | 3/1992 | Aita et al. | 606/5 X |
| 5,125,926 | 6/1992 | Rudko et al. | 606/12 |
| 5,147,354 | 9/1992 | Boutacoff et al. | 606/15 |
| 5,380,316 | 1/1995 | Aita et al. | 606/7 |
| 5,389,096 | 2/1995 | Aita et al. | 606/7 |
| 5,554,152 | 9/1996 | Aita et al. | 606/7 |

OTHER PUBLICATIONS

Jeevanandam et al. "Myocardial Revascularization by Laser–Induced Channels," *Surgical Forum* XLI, 225–227 (Oct. 1990).

Hardy et al. "Regional Myocardial Blood Flow and Cardiac Mechanics in Dog Hearts with CO2 Laser–Induced Iniramyocardial Revascularization" *Basic Res. Cardiol.* 85:179–197 (1990).

Mirhoseini et al., "Clinical and Histological Evaluation of Laser Myocardial Revascularization" *Journal of Clinical Laser Medicine & Surgery*, 73–78 (Jun. 1990).

Mirhoseini,et al, "Laser in Cardiothoracic Surgery" *Lasers in General Surgery* (Joffe, Editor), Williams and Wilkins, 216–232 (1989).

Mirhoseini et al. "New Concepts in Revascularization of the Myocardium" *A Thorac. Surg.* 45:415–420 (Apr. 1988).

Walter et al. *Europ. Surg. Res.* 3:130–138 (1971).

Mirhoseini et al. Clinical Report: "Laser Myocardial Revascularization" *Lasers in Surgery and Medicine* 6:49–461 (1986).

Mirhoseini et al. "Myocardial Revascularization by Laser: A Clinical Report" *Laser in Surgery and Medicine* 3:241–245 (1983).

(List continued on next page.)

*Primary Examiner*—Michael Peffley
*Attorney, Agent, or Firm*—Heller Ehrman White & McAuliffe

[57] ABSTRACT

The method for intra-operative myocardial revascularization of a human heart includes a inserting a portion of an elongated flexible lasing apparatus into the chest cavity of a patient, and lasing channels from the epicardium through the myocardium of the heart, without mechanical tearing of the heart tissue. The apparatus is guided to an area exterior to a ventricle of the patient's heart, and the distal end of the optical fiber apparatus is directed to an area of interest where the exterior wall of the heart is irradiated with laser energy to form a channel through the myocardium.

6 Claims, 1 Drawing Sheet

OTHER PUBLICATIONS

Mirhoseini et al. "Revascularization of the Heart by Laser" *Journal of Microsurgery* 253–260 (Jun. 1981).

Mirhoseini et al. "Transvenicular Revascularization by Laser" *Lasers in Surgery and Medicine* 2:187–198 (1982).

Mirhoseini "Laser Applications in Thoracic and Cardiovascular Surgery" *Medical Instrumentation,* 17(6): 401–403 (Nov./Dec. 1982).

Mirhoseini "Laser Revascularization of the Heart" *New Frontiers in Laser Medicine and Surgery* (Atsumi, Editor), ISBN Elsevier Science Publishing Co., 296–303 (1982).

METHOD FOR INTRA-OPERATIVE MYOCARDIAL REVASCULARIZATION

This is a continuation application of application Ser. No. 08/361,787, now U.S. Pat. No. 5,554,152, which was filed on Dec. 20, 1994, which is a continuation of Ser. No. 08/079,699, filed on Jun. 16, 1993, now U.S. Pat. No. 5,380,316, which is a continuation of Ser. No. 07/630,259, filed on Dec. 18, 1990 (now abandoned).

FIELD OF THE INVENTION

This invention is generally directed to the field of laser surgery, and more particularly to laser surgery procedures to improve the flow of blood to the heart muscle.

BACKGROUND OF THE INVENTION

The number and variety of medical methods available to repair the effects of cardiovascular disease has increased rapidly over the last several years. More particularly, alternatives to open heart surgery and cardiovascular by-pass surgery have been extensively investigated, resulting in non-surgical procedures such as percutaneous transluminal coronary angioplasty, laser angioplasty, and atherectomy. These procedures are primarily directed toward the reduction of stenosis within the vasculature of a patient by either expanding the lumen through the use of a balloon, or ablating or otherwise removing the material making up the stenosis.

While these procedures have shown considerable promise, many patients still require bypass surgery due to such conditions as the presence of extremely diffuse stenotic lesions, the presence of total occlusions and the presence of stenotic lesions in extremely tortuous vessels. Also, some patients are too sick to successfully undergo bypass surgery, and because the above treatments require surgical backup in the case of complications, they are untreatable. Some patients requiring repeat bypass surgeries are also untreatable.

One alternative to these procedures is known as Laser Myocardial Revascularization (LMR). In LMR, channels are formed in the ventricle wall with a laser. These channels provide blood flow to ischemic heart muscle. A history and description of this method is presented by Dr. M. Mirhoseini and M. Cayton in "Lasers in Cardiothoracic Surgery" in *Lasers in General Surgery* (Williams & Wilkins; 1989) pp. 216–223.

In the procedure described therein, a $CO_2$ laser is used to produce channels in the ventricle from the epicardium through to the myocardium. This procedure follows a surgical cutdown. External pressure is used to stop bleeding from the ventricle to the outside. Dr. Mirhoseini has documented that although the channel is sealed at the epicardial layer, it remains patent in the endocardial and myocardial layers. Laser energy is transmitted from the laser to the epicardium by means of an articulated arm device that is commonly used for $CO_2$ laser surgery.

A proposed improvement in the design is described in Hardy—U.S. Pat. No. 4,658,817. A needle is added to the distal tip of the articulated arm system, with laser energy passing through the lumen of the needle. The metal tip of the needle of the device is used to pierce most of the myocardium and the laser beam is used to create the desired channel through the remaining portion of the myocardium and through the adjacent endocardium.

Hardy contends that mechanical piercing serves to facilitate sealing of the epicardial portion of the channel. Mechanical piercing is highly undesirable, because such piercing always entails some degree of tearing of the pierced tissue. Tearing leads to fibrosis as the mechanical tear heals. Fibrosis severely diminishes the effectiveness of the LMR treatment.

These LMR procedures still require that the chest wall be opened in order to access the heart muscle with presently utilized laser devices. Thus these procedures require major surgery which is highly invasive and which may result in severe complications.

An additional problem associated with those procedures utilizing an articulated arm device is that the articulated arm is difficult to manipulate. Thus portions of the heart may be effectively unreachable by the device.

Broadly, it is the object of the present invention to provide an improved method for performing laser myocardial revascularization.

It is a further object of the present invention to provide a less invasive method for performing laser myocardial revascularization.

It is a still further object of the present invention to provide a method for performing laser myocardial revascularization which can access difficult to reach portions of the heart.

It is a yet further object of the present invention to provide a method for performing laser myocardial revascularization which does not require mechanical perforation of heart tissue.

These and other objects of the present invention will be apparent to those skilled in the art from the following detailed description and the accompanying drawings.

SUMMARY OF THE INVENTION

The present invention comprises a method of intra-operative myocardial revascularization of the myocardium of the heart of a patient. An elongated flexible lasing apparatus is inserted into the chest cavity of the patient. The distal end of the lasing apparatus is then guided to an area immediately adjacent and exterior to the patient's heart. The exterior wall of the heart is next irradiated with laser energy emitted from the distal end of the lasing apparatus with sufficient energy and for a sufficient time to cause a channel to be formed from the exterior surface of the epicardium through the myocardium and the endocardium. An exterior portion of the channel is then sealed.

DETAILED DESCRIPTION OF THE PREFERRED EMBODIMENT

Figure 1:
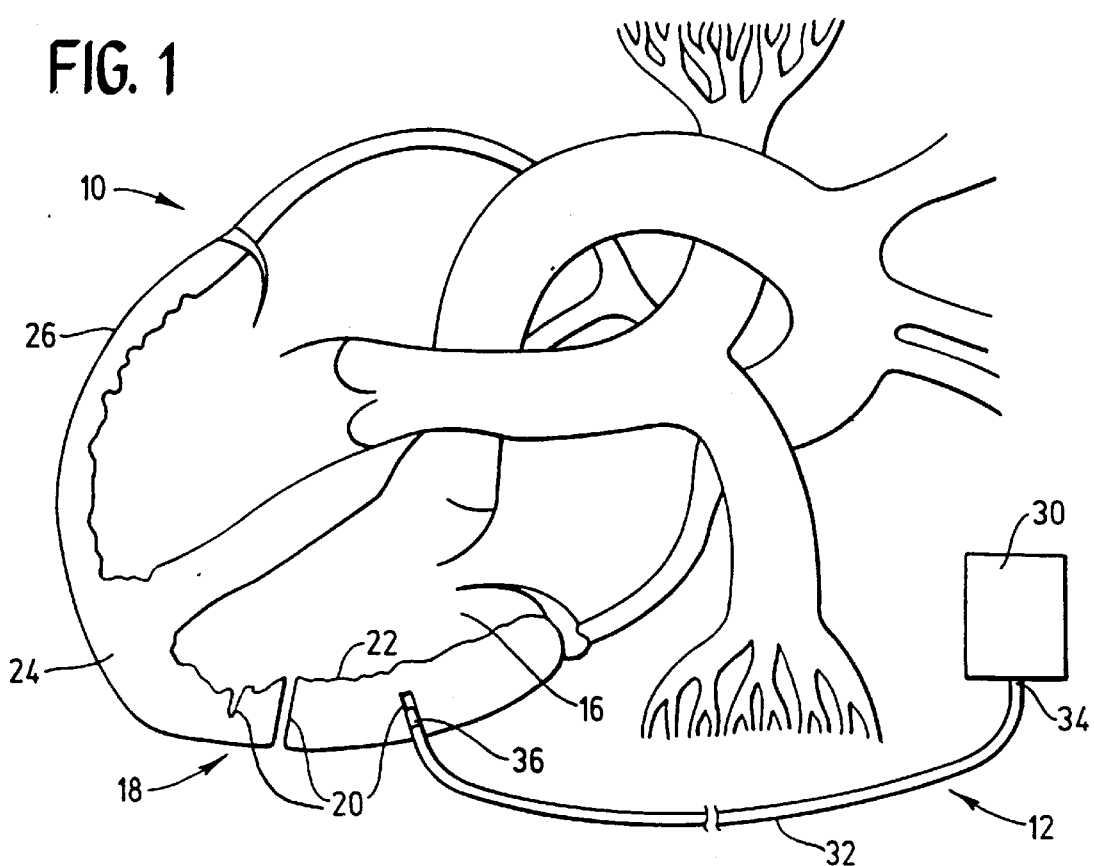
FIG. 1 is a schematic section of a human heart showing revascularization of the myocardium according to the invention.

As is shown in the drawings, which are provided for purposes of illustration and not by way of limitation, an apparatus suitable for implementing the present invention is embodied in a system for revascularization of the myocardium of a human heart 10. As is illustrated in FIG. 1, the elongated flexible lasing apparatus 12 is placed adjacent to an area such as a ventricle 16 having an area 18 in need of increased blood circulation due to cardiovascular disease. Lasing apparatus 12 may include either an optical fiber adapted to a laser or a waveguide adapted to a $CO_2$ laser or other laser. Portions of the heart other than ventricles might also be revascularized by this method. A number of channels 20 can be formed by the shapeable elongated flexible lasing apparatus from the outer wall, or epicardium 26, and extend a through the myocardium 24 and perforating the interior of the heart wall, the endocardium 22.

The elongated flexible lasing apparatus 12 includes a remotely located source of laser energy 30 connected to the proximal end 34 of an optical fiber 32. Laser 30 may typically be a $CO_2$ laser, or an HO YAG laser, for example, although other sources of energy, such as excimer lasers, are adaptable to the invention. $CO_2$ lasers would require an appropriate optical waveguide 32. Optical fiber 32 conducts the laser energy to its distal end 36.

Figure 2:
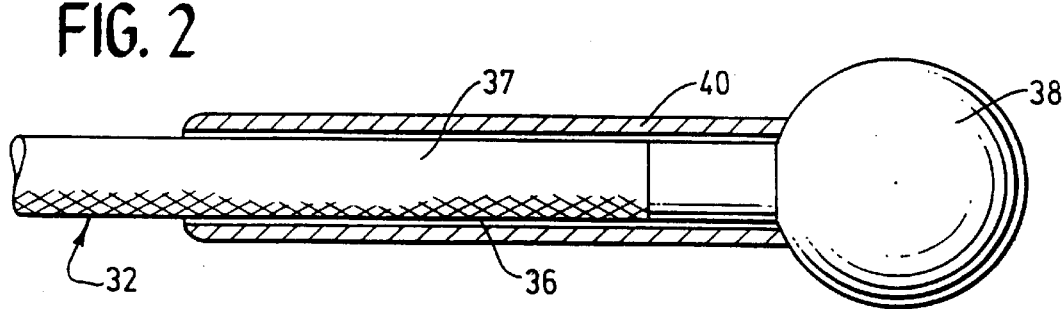
FIG. 2 is a schematic cross-section of an elongated flexible lasing apparatus suitable for the method of the invention.
Figure 3:
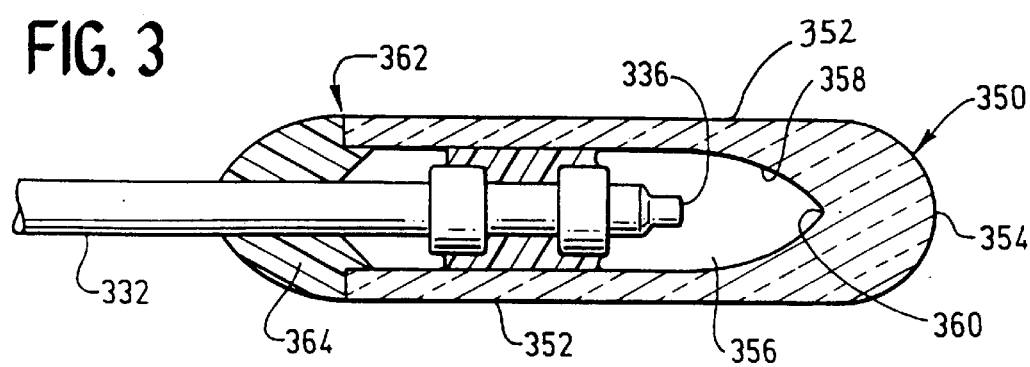
FIG. 3 is a cross-section of a preferred lens design for the invention.

Referring to FIG. 2, a lens 38 having a sleeve 40, is preferably connected to the distal end 36 of optical fiber 32. Although lens 38 is illustrated in FIG. 2 as being a ball type lens, the preferred embodiment of lens 38 is illustrated in FIG. 3, which is discussed below. Lens 38 controls the output spatial distribution of the laser energy emitted by optical fiber 32.

In a preferred embodiment of an apparatus adapted for the present method, a portion of distal end 36 of optical fiber 32 is adapted to be shaped into a desired configuration. Such a shapeable fiber apparatus is disclosed in co-pending application U.S. Ser. No. 07/605,774 by Samson, assigned to Advanced Cardiovascular Systems. A tubular metallic braid 37 (only shown is part) is placed over and affixed to a section of distal end 36 of optical fiber 32. This allows optical fiber 32 to retain its shape in a desired configuration.

Referring to FIG. 3, it has been found that in a preferred embodiment of the invention, a lens 350 is configured to include an essentially cylindrical outer surface 352 terminating in a convex distal tip 354. An optical fiber 332 extends into an internal cavity 356 and terminates in a position spaced apart from an internal aspheric or ogival shaped surface 358, the cavity apex 360 of which is distal from distal end 336 of fiber 332. The interface 362 between optical fiber 332 and lens 350 is reinforced, preferably with epoxy 364 or the like, although other means of reinforcement designed to prevent dislodging of the lens are adaptable to the invention.

The basic method of the present invention has been laid out above. The shapeable elongated flexible lasing apparatus 12 is inserted into the chest cavity. This insertion may require only a small incision, which would minimize the invasiveness of the procedure. Lasing apparatus 12 is then placed adjacent an area such as a ventricle 16 having an area 18 in need of increased blood circulation due to cardiovascular disease. This placement may be facilitated by shaping the fiber into a desired configuration. A number of channels 20 can then be formed by the shapeable elongated flexible lasing apparatus 12 from the outer wall, or epicardium 26, and extend through the myocardium 24 and perforating the interior of the heart wall, the endocardium 22.

In operation, the distal end of the optical fiber apparatus may be maintained in position on the outer heart wall by a gentle pressure, to insure that the apparatus is not dislodged in the formation of the channel between pulses of the laser. The heart beat is preferably monitored, and the laser is preferably gated to generate one or more pulses during contractions (systole) of the heart, and to generate no pulses during the rest of the heart cycle. These procedures combine to anchor the apparatus to a relatively stable location on the tissue that is to be ablated.

In early experiments with a HO laser, it was found that it may be desirable to begin the procedure with approximately 0.65 j pulses, at a frequency of at least 2 Hz, in order to penetrate the endocardium, and then decrease the laser power to approximately 0.2 j to form the channel in the myocardium. This minimizes the need for anchoring the catheter to the area to be treated. Note that the dosimetry is dependent upon the diameter of the lens used.

In practice, it has been found that the lens of the embodiment of FIG. 3, when in contact with tissue, cuts a lumen equal or greater than the lens diameter which is in front of and axially aligned with the axis of the lens. This provides improved ablation of channels into the heart muscle of the type preferred in this method. As the channel is cut, the cylindrical outer surface 352 assists in guiding and controlling the catheter during the cutting process. The angle of the projected energy from the lens can also be controlled by some degree with the separation of distal tip 336 of optical fiber 332 from the cavity distal apex 360. It has also been found that the construction is scalable.

It has been found that channels that are approximately 1.5 mm–2.0 mm in diameter and approximately 1 to 3 cm deep may easily and efficiently be cut by this method, and that the revascularization procedure dramatically improves the flow of blood to the heart muscle, thereby decreasing the probability of heart attack from occlusion of the external vasculature of the heart.

There has been described herein a method of performing laser revascularization of the heart. Various modifications to the present invention will become apparent to those skilled in the art from the foregoing description and accompanying drawings. Accordingly, the present invention is to be limited solely by the scope of the following claims.

What is claimed is:

1. A minimally invasive procedure for increasing blood flow to a region in an outer ventricular wall of a patient's heart, comprising;
   a) providing an elongated flexible energy delivering device having an elongated shaft, a proximal end, a distal end and a surface on the distal end configured for emission of energy to ablate tissue in the outer ventricular wall of the patient's heart;
   b) introducing a distal portion of the elongated flexible energy delivering device into the patient's chest through a small opening therein;
   c) directing the distal portion of the elongated flexible energy delivering device within the patient's chest cavity until the surface configured to emit energy at the distal end of the device contacts the outer ventricular wall; and
   d) emitting energy from said surface to ablate tissue in the outer ventricular wall of the patient's heart.

2. The procedure of claim 1 further including contacting said ventricular wall with the energy emitting surface in a plurality of locations to ablate tissue in the ventricular wall at the plurality of locations.

3. The procedure of claim 1 further including the steps of directing laser energy from a source thereof through the elongated flexible energy delivering device to the distal end thereof and controlling the emission of laser energy from said distal end to form a laser beam which penetrates into the ventricular wall and ablates tissue therein.

4. The procedure of claim 3 wherein laser energy is directed through the elongated energy delivering device and a lens at the distal end of the device controls the emission of laser energy.

5. A minimally invasive procedure for increasing blood flow to a region in an outer ventricular wall of a patient's heart, comprising:
   a) providing an elongated flexible energy delivering device having a distal end and a surface at the distal end to emit energy which penetrates into the outer ventricular wall of the patient's heart ablating tissue therein;
   b) introducing a distal portion of the elongated flexible energy delivering device with the surface to emit energy at the distal end into the patient's chest through a small opening therein;
   c) directing the distal portion of the elongated flexible energy delivering device within the patient's chest cavity until the surface to emit energy at the distal end thereof contacts the exterior of the ventricular wall; and
   d) penetrating the outer ventricular wall of the patient's heart at least into a myocardial layer with energy emitted from said energy emitting surface to ablate tissue at least in the myocardial layer.

6. A minimally invasive procedure for treating a region of an outer ventricular wall of a patient's heart, comprising;
   a) providing an elongated flexible energy delivering device having an elongated shaft, a proximal end, a distal end and a surface at the distal end to emit energy to ablate tissue;
   b) introducing into a cavity of the patient's chest through a small opening therein a distal portion of the elongated flexible energy delivering device with the means at the distal end to emit energy;
   c) directing the distal portion of the elongated flexible energy delivering device within the patient's chest cavity until the surface to emit energy at the distal end contacts the exterior of the outer ventricular wall; and
   d) emitting energy to ablate tissue in the myocardium of the outer ventricular wall of the patient's heart.

* * * * *